United States Patent
Van Pelt et al.

[11] Patent Number: 5,879,948
[45] Date of Patent: Mar. 9, 1999

[54] DETERMINATION OF TOTAL MERCURY IN EXHAUST GASES

[75] Inventors: Vincent J. Van Pelt, Tuscumbia; Sandra J. Meischen, Florence, both of Ala.

[73] Assignee: Tennessee Valley Authority

[21] Appl. No.: 854,367

[22] Filed: May 12, 1997

[51] Int. Cl.$^6$ ........................... G01N 33/20; G01N 21/01
[52] U.S. Cl. ............... 436/81; 436/73; 436/155; 436/158; 436/181; 436/182; 422/50; 422/62; 422/78; 422/80; 422/81; 422/82.09; 422/93; 250/373; 73/23.31
[58] Field of Search .................. 436/73.81, 155, 436/158, 160, 177, 181, 182; 422/50, 62, 78, 80, 81, 82.09, 83, 91, 93; 250/372, 373; 23/23.31

[56] References Cited

U.S. PATENT DOCUMENTS

| | | | |
|---|---|---|---|
| 3,826,614 | 7/1974 | Capuano | 436/81 X |
| 3,826,618 | 7/1974 | Capuano | 436/81 X |
| 3,884,639 | 5/1975 | Sugiyama | 436/81 |
| 4,758,519 | 7/1988 | Nakao et al. | 436/81 |
| 5,277,056 | 1/1994 | Braun et al. | 73/23.31 |
| 5,679,957 | 10/1997 | Durham et al. | 250/373 |

FOREIGN PATENT DOCUMENTS

| | | | |
|---|---|---|---|
| 278096 | 8/1988 | European Pat. Off. | 436/81 |
| 4143170 | 7/1993 | Germany . | |
| 52-11094 | 1/1977 | Japan | 46/81 |
| 63-191059 | 8/1988 | Japan . | |

OTHER PUBLICATIONS

G. J. Korinek et al. *Can. J. Chem.* 1956, 34, 1372–1381.
W. A. Oates et al. *Chem. Abstr.* 1962, 57, 14470d.
B. Hall et al. *Environ. Sci. Technol.* 1990, 24, 108–111.
A. D. Sappey et al. *Prepr. Pap.—Am. Chem. Soc. Div: Fuel. Chem.* 1995, 40, 818–822.
J. Wang et al. *Water, Air, Soil Pollut.* 1995, 80, 1217–1226.
R, Zepeck eta, "Continuous Emission Monitoring; Total Mercury Analysis" Waste Combust. Boilers Ind. Furn., Proc. Spec. Conf. 1996, Air & Waste Management Association: Pittsburgh, PA, pp. 137–142.

*Primary Examiner*—Arlen Soderquist
*Attorney, Agent, or Firm*—Robert A. Petrusek

[57] ABSTRACT

The present invention relates to a system, apparatus, and process to reduce the oxidized mercury in an exhaust gas to elemental mercury and to prevent its reoxidation by congeneric components in the exhaust gas prior to the photometric measurement of said elemental mercury. In the process, the sample stream flows through a reactor heated to preferably about 800° C. in which a stream of hydrogen is introduced directly into a hot portion thereof. The congeneric oxidized mercury species, i.e, $HgCl_2$, and HgO are thermally reduced quantitatively to elemental mercury. The hydrogen reacts in situ with oxygen to form water vapor and with chlorine to form hydrochloride gas. The hydrochloride gas is effectively absorbed by the water vapor and consequently prevents the reoxidation of elemental mercury. The concentration of total mercury in a stream can then be determined by the intensity of radiation absorbed by a UV spectrometer.

9 Claims, 1 Drawing Sheet

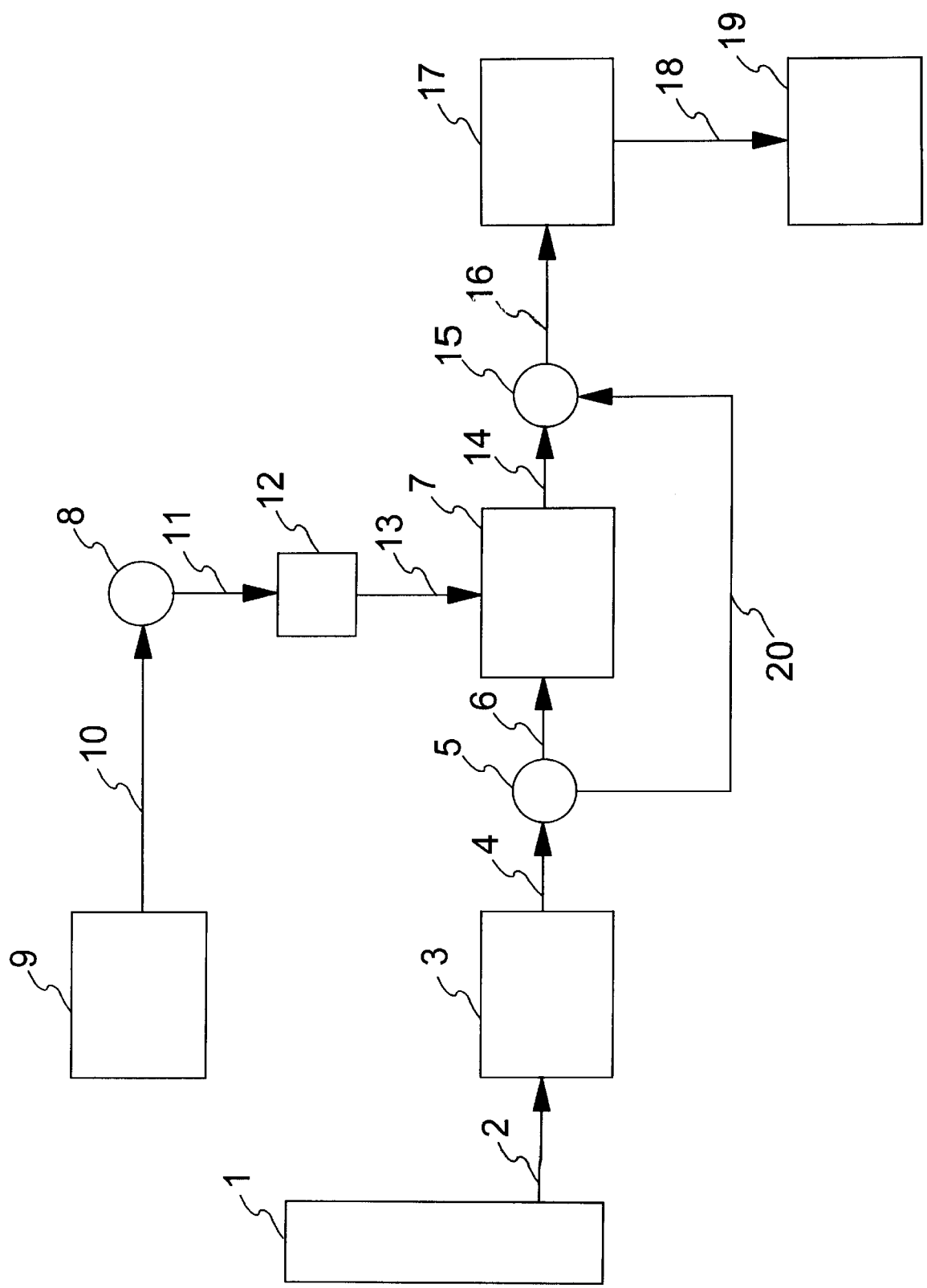

DETERMINATION OF TOTAL MERCURY IN EXHAUST GASES

The invention herein described may be manufactured and used by or for the government for governmental purposes without the payment to us of any royalty therefor.

INTRODUCTION

The present invention relates to measurement of mercury emitted by combustion sources and consequently the contribution of combustion sources to the mercury global cycle. Mercury from natural and anthropogenic sources recycles in the environment and collects in terrestrial and aquatic species, ultimately acting as a toxic exposure source in the food web. Numerous states have reported increases in fish advisories attributable to accumulated mercury sources. Mercury is listed as a hazardous air pollutant (HAP) in Title III of the Clean Air Act Amendments of 1990 for which EPA is mandated to evaluate emissions and health risks. The Draft EPA Mercury Study Report to Congress estimates the total annual input of mercury emissions from anthropogenic sources globally is 4,000 tons with 200–300 metric tons emitted in the U.S. The report identifies the largest sources of mercury emissions in the U.S. to be incinerators which combust mercury-containing wastes (municipal and medical), and utility, commercial, and other boilers that combust fossil fuels. Other potentially important sources of mercury emissions are manufacturing plants and hazardous waste incinerators. Sixty percent of DOE's hazardous waste contains mercury. Regulatory guidelines for mercury emissions from municipal waste combustors were published by EPA in 1995. Guidelines are expected to be released in 1997 for operation of medical waste incinerators and hazardous waste incinerators. Mercury emissions from coal-fired combustors will be addressed in EPA plans to be announced in 1998. More restrictive controls on air toxics will undoubtedly result in higher operational costs for these industries. Accordingly, there exists a real and eminent need for development of a simple, low cost, accurate technology to measure mercury species and total mercury in real-time. A total mercury measurement is required for regulatory monitoring, whereas the evaluation of mercury control technologies and manufacturing processes requires measurements that reveal the distribution of elemental and oxidized mercury.

BACKGROUND OF THE INVENTION

1. Field of the Invention

This invention relates to an apparatus and process for its operation which prevents the reoxidation of elemental mercury in gaseous matrices containing oxidizing compounds following the thermal reduction of oxidized mercury to elemental mercury. Such gaseous matrices are found, for example, in exhaust emissions of coal-fired boilers or incinerators. In particular, the apparatus, process and operation of the present invention may be employed in the analysis of total mercury in continuous emissions monitors used for regulatory compliance or process control measurements.

2. Description of the Prior Art

Various approaches in the development of continuous emissions monitors (CEMs) for mercury measurement in flue gas emissions to determine the elemental mercury therein, Hg(O), have included both a UV photometric method and an Atomic Absorption method. These methods detect and measure amounts of elemental or reduced mercury, Hg(O), at excitation wave lengths of 254 nm but unfortunately, any oxidized species of mercury therein cannot likewise be measured. In order to measure total mercury, the oxidized mercury species state must first be reduced to Hg(O). The predominant form of oxidized mercury existing in the flue gas coal fired combustors, waste combustors, and incinerators is $HgCl_2$ [C. S. Krivanek, III, Journal of Hazardous Materials, 47 (1996) *Mercury Control Technologies for MWC's: The Unanswered Questions*, pp. 119–136] and [IEA Coal Research, *Mercury Emissions and Effects—The Role of Coal*]. By measuring the elemental mercury concentration in a gaseous matrix prior to and subsequent to a mercury reduction process, the total mercury concentration and the distribution of oxidized and reduced mercury can be determined. The determination of this distribution is essential to the development of effective mercury control options for gaseous emissions and can have value to effective process quality control. As used herein, the terms "elemental mercury," "metallic mercury," "reduced mercury" and "Hg (O)" all mean and refer to the same form of mercury.

Typically, in order to measure the total mercury concentration of a sample by laboratory analysis, the reduction of oxidized mercury involves the mixing of a gas or liquid sample with reducing solutions prior to measurement of Hg(O). In the development of on-line continuous emissions monitors (CEMs) for mercury measurement in the exhaust gasses of flue stacks, several instrument manufacturers have incorporated reducing solutions into their on-line processes. These devices rely on reducing solutions such as sodium hydroboride solution, stannous chloride solution or other reducing solutions to convert oxidized mercury to Hg(O) prior to measurement by a detector such as a ultraviolet (UV) or atomic absorption (AA) detector. An obvious disadvantage to this type of instrument design is that it requires frequent solution replenishment.

For continuous on-line measurement, a dry mercury reduction method is preferable to a wet one, since there are fewer maintenance requirements which, in turn, translates to a more reliable technique. Thermal reduction of oxidized mercury is such an alternative dry method, it being reported in the open literature that oxidized mercury can easily be reduced at temperatures of about 800° C. However, a gaseous exhaust from a coal-fired boiler or incinerator may oftentimes contain oxidizing agents that can and will reoxidize the thermally reduced mercury before a mercury measurement can be effected.

The fossil-fueled and waste combustion industries generate gaseous mixtures which typically contain compounds such as NOx, $O_2$, $H_2O$, $CO_2$, and CO. Other gases such as $SO_2$, HCl, $Cl_2$, $H_2S$ and $NH_3$ and volatile metals and organics also may be present depending on the type of fuel combusted. Flue gases resulting from operation of coal combustors typically contain $O_2$, $CO_2$, CO, NO, $NO_2$, $SO_2$, HCl, $N_2O$, $H_2O$ and mercury species as well as many trace components. Work leading to the instant invention determined that, of the components, supra, which are typically found in flue gas which have the greatest effect on the reoxidation of elemental mercury are, hydrochloride gas and oxygen. Furthermore, hydrochloride gas has the greatest effect on the reoxidation of mercury. Furthermore, it was found that the presence of oxygen in admixture with HCl gas acts to enhance the hydrochloride effect on elemental mercury oxidation.

The effect of hydrochloride on the reoxidation of elemental mercury upon thermal reduction is also reported by Wang, Xiao and Lindqvist, "Water, Air and Soil Pollution" 80: 1217–1226, 1995. They used crushed quartz chips to fill a quartz cell and thereafter heated their cell to 850°–900° C. to reduce Hg (II) in a gaseous stream. They also found the addition of HCl to the gaseous matrix negated the converter effect. Their approach to counter the HCl effect was to fill the converter with basic materials. Filling the quartz converter cell with a layer of soda lime or sodium carbonate or of crushed quartz treated with NaOH solution did improve the overall conversion efficiency by reacting the basic materials filling the conversion tube with hydrochloride (HCl) gas and preventing the reoxidation of elemental mercury. The effectiveness of this approach was limited however due to the severe corrosive nature of the basic solids and the high temperatures necessary for the conversion which they reported destroyed their converter cells within two days.

In view of the consideration and problems, supra, it should be appreciated by those skilled in this art that there is a definite need for a simple, reliable method to accurately measure and speciate mercury in the exhaust streams of flue stacks in real time at various waste and fossil-fueled combustors to measure mercury emissions and assist in identifying effective control technologies.

SUMMARY OF THE INVENTION

The present invention relates to a new, novel, and unique apparatus and a process for effecting the thermal reduction of oxidized mercury in an exhaust gas matrix to metallic mercury and further, it relates to the maintenance of the resulting metallic mercury oxidation state prior to the photometric measurement of total mercury in such exhaust matrix.

Many of the principal objects of the instant invention, which are more succinctly stated later, are effected by the instant, new, and novel apparatus and process which is far more flexible and is substantially less complicated than are prior art solution systems heretofore utilized for the reduction of mercury species to metallic mercury and are much more easily incorporated into existing and commercially available measurement systems of the type presently used for total mercury in exhaust gases. The reactor or reactor means of the present invention includes: (a) a first conduit having an inlet for the input gas stream and an outlet for said gas stream after reduction of oxidized mercury to Hg(O); (b) a second conduit disposed within the input gas stream first conduit, said second conduit having an inlet for a hydrogen stream proximal to the inlet for the first conduit with an outlet for the second conduit at a defined hot zone where the hydrogen in the second conduit is mixed with the inlet gas from the first conduit; (c) heating means for selectively elevating the temperature within such defined reactor hot zone to thereby simultaneously reduce oxidized Hg to metallic mercury, to react hydrogen with oxygen to form water vapor, and to react hydrogen with chlorine to form hydrochloride gas, after which the gas sample containing such reactant is sent to the condensing means for removal of water vapor, which is HCl laden prior to its introduction into the detection means.

The instant, new, and novel process of the present invention is based on the following observations which were made in our work with simulated flue gases at temperatures ranging from about 100° C. to about 150° C.: (1) Hydrochloride gas and chlorine oxidize metallic mercury in a nitrogen atmosphere, (2) the addition of oxygen to the gaseous mix further increased the oxidation of elemental mercury, and (3) up to about 300 ppm hydrochloride gas in the presence of about 1–15% water vapor did not oxidize the ppb metallic mercury present therein, but rather preferentially associated with the water vapor. The concept underlying the gist of the present invention is to prevent reoxidation of metallic mercury by adding water vapor to the reactor zone. The specific approach of the instant invention is to produce the water vapor in situ within the hot zone of the reactor by adding hydrogen directly to the oxygen-containing flue gas sample introduced into the reactor, thereby removing oxygen therefrom. The instant process also ensures that any chlorine gas present in the reactor zone is converted in the hot zone thereof to hydrochloride gas, it being appreciated that the quantity of said chlorine gas is usually two to three orders of magnitude less than the oxygen in such flue gas. The water vapor produced therein scrubs the hydrochloride gas from the gas stream and prevents an interaction with the elemental mercury. Consequently, by adding the hydrogen reactant directly into predetermined portions of the reactor, i.e., the hot zone, water vapor is formed which effectively scrubs hydrochloride gas from the reactor and prevents the reoxidation of the metallic mercury formed during thermal reduction of oxidized mercury.

Continuous Hg(O) determination in exhaust gases comprises: (a) continuously removing a gas sample to be analyzed from the flue, or other gas stream which is usually effected by use of a heated extractive probe; (b) introducing the removed sample through a filtering device to remove particulates therefrom; (c) introducing the particulate free gas sample into a thermal conversion reactor, hereafter simply reactor or reactor means (in our early laboratory work one such conversion reactor conveniently comprised an insulated quartz tube wound with heating element, such as Nichrome® elements so as to raise the temperature of gaseous components therein to a temperature in the range of from about 800° C. to 900° C., and wherein the gaseous flow path is arranged to provide in the hot zone of the reactor a residence time at such elevated temperature of from about 1 to about 4 seconds), whereby the oxidized Hg in the sample is reduced to metallic Hg; (d) simultaneously introducing a stream of hydrogen into the hot zone of a reactor whereby the oxygen in the hot zone reacts with such introduced hydrogen to thereby form water vapor and further wherein additional amounts of such introduced hydrogen reacts with any chlorine therein to thereby form hydrochloride gas (again, in our early laboratory work such introduction of the hydrogen stream was conveniently effected by introducing same into the reactor hot zone comprised of a second quartz tube, smaller in diameter than the quartz tube comprising the outer shell of the reactor zone and maintained substantially concentric therein); (e) introducing the resulting partially reduced gas to a condenser, wherein the resulting water vapor, including any hydrochloride gas contained therein is removed therefrom; and (f) introducing the resulting substantially $H_2O$ and HCl depleted gas mixture to a photometer, wherein the desired determination of Hg(O) takes place. Note: Any reference made herein to materials and/or apparatus which are identified by means of trademarks, trade names, etc., are included solely for the convenience of the reader and are not intended as, or to be construed, an endorsement of said materials and/or apparatus.

OBJECTS OF THE INVENTION

It is therefore the principal object of the present invention to provide a relatively simple and uncomplicated, low cost, flexible apparatus and process for its operation which allows for the measurement of total mercury in a flue gas sample by eliminating the oxidative effect of congeneric components of the flue gas upon thermal decomposition of mercury species to elemental mercury.

A further object of the instant invention is to provide a flexible method and means which may be incorporated into any continuous emissions monitor for the photometric measurement of total mercury.

A still further object of the instant invention is to provide a process which may be effectively utilized to reduce all mercury species to the elemental form as a component of a sensor system configured to monitor total, elemental, and ionic mercury in gases emitted from combustion of natural and anthropogenic sources.

Still further and more general objects and advantages of the present invention will appear from the more detailed description set forth below, it being understood, however, that this more detailed description is given by way of illustration and explanation only, and not necessarily by way of limitation since various changes therein may be made by those skilled in the art without departing from the true spirit and scope of the present invention.

DESCRIPTION OF THE DRAWING

The present invention, together with further objectives and advantages thereof, will be better understood from a consideration of the following description taken in connection with the accompanying drawing in which:

The FIGURE is a flowsheet generally illustrating the principles of the instant, new, and novel method and means for removing the effect of oxidizing agents on the conversion of oxidized mercury species to elemental mercury prior to photometric measurement of mercury in flue gas streams.

To measure total mercury in a flue gas by the instant process, all mercury species in the sampled flue gas must be converted to elemental mercury prior to the introduction to spectrophotometer which conversion is accomplished in the following manner.

Referring now more specifically to the FIGURE, a sample of the flue gas is removed from exhaust stack 1 by heated probe 2 and delivered to heated filter means 3 where any particulate matter therein is removed. Heated line 4 transports the flue gas removed from filter means 3 to transfer valve 5, which (during the measurement of total mercury) directs the flue gas to heated line 6 which delivers the flue gas to reactor zone 7 via heated line 6. Also, during the measurement of total mercury, valve 8 is open allowing hydrogen from storage means 9 to pass through lines 10 and 11 to flow controller 12. Flow controller 12 controls the rate at which hydrogen passes through line 13 into reactor zone 7. The high temperature in reactor zone 7 causes the mercury chloride in the flue gas introduced therein to decompose into elemental mercury and chlorine. The hydrogen introduced into reactor zone 7 via line 13 is introduced into the hot zone (not shown, but understood to be located generally within the center portion of reactor zone 7) where it reacts with the oxygen and chlorine contained in the flue gas introduced via line 6 and thereby prevents said oxygen and chlorine from interfering with the complete conversion in the hot zone of reactor zone 7 of mercury chloride to elemental mercury therein. Heated line 14 directs the flue gas leaving reactor zone 7 to transfer valve 15 which directs the flue gas by way of heated line 16 to an electrically cooled unit 17 which condenses and removes water, which water is laden with any HCl formed in situ, supra, in said hot zone from the flue gas. Heated line 18 then transports the resulting water and hydrogen chloride depleted flue gas to spectrophotometer 19 which measures the elemental mercury in the flue gas. Alternatively, the contribution of elemental mercury to the total mercury in the flue gas can be determined in the following manner. A sample of flue gas is removed from stack 1 by heated probe 2 and delivered to heated filter assembly 3 where any particulate matter therein is removed. Heated line 4 transports the flue gas to transfer valve 5, which transfer valve 5 directs the flue gas to heated line 20 which by-passes reactor zone 7 and sends the flue gas directly to transfer valve 15 which directs the flue gas by way of heated line 16 to an electrically cooled unit 17 which condenses and removes the water from the flue gas. The heated line 18 then transports the flue gas to spectrophotometer 19 which measures the mercury originally present in its elemental form in the flue gas.

DESCRIPTION OF THE PREFERRED EMBODIMENTS

The present invention utilizes a combination of the reaction properties of materials including the property of $HgCl_2$ to thermally decompose to $Hg(O)$ and $Cl_2$ at about 750° C. or above and preferably between about 800° C. and 1000° C., the property of hydrogen to react with oxygen and form water vapor, the property of hydrogen to react with $Cl_2$ and form HCl, and the property of water vapor to collect, by absorption, hydrochloride gas. This invention, including methods, means, processes and techniques thereof is based on the instant new discovery that the presence of water vapor in an exhaust gas will interfere with the oxidation of $Hg(O)$ by gaseous oxidants, such as hydrochloride gas, by absorbing same with water vapor. The thermal reduction of mercury (II) chloride to metallic mercury in a gaseous matrix also produces the oxidant, chlorine. Chloride, whether in the form of chlorine or hydrochloride gas, is a potent oxidant for $Hg(O)$ and its effect is substantially magnified in the presence of oxygen. Therefore, in the practice of this instant invention, during the thermal reduction of mercury, water vapor is formed in situ and thereby indirectly added to the sample stream to thereby prevent the reoxidation of metallic mercury. The water vapor is generated in situ by introducing predetermined amounts of hydrogen gas into the reactor hot zone. The hydrogen thereby introduced reacts with oxygen to form water vapor and coincidentally reacts with any free chlorine gas (usually some two to four orders of magnitude less than said oxygen) therein to form hydrochloride gas. Consequently, the oxidizing effect of oxygen is removed from the reaction system by the formation of water vapor which resulting water vapor acts to scrub still another mercury oxidant therein, hydrochloride gas, from the gas stream.

In order to achieve the foregoing and other objects of the instant invention, the present invention provides a method and means for reducing oxidized mercury to $Hg(O)$ in a gaseous matrix which contains oxidizing agents such as hydrochloride gas. The process comprising the steps of: (a) obtaining a sample, preferably in the form of a continuous stream of waste gas as, for example, from an incinerator or waste combustor; (b) removing any particulates from such sample as, for example, preferably, but not necessarily by filtration; (c) directing the gas flow into reactor zone having a length, size, and configuration so as to ensure that the gas introduced thereinto is maintained at a temperature of at least 800° C. for a residence time of at least about 1 second and further disposed so as to feed hydrogen directly into said reactor zone; (d) thereafter, removing from the sample, the water and water-soluble components from said sample; and (e) subsequently measuring the UV radiation intensity of the resultant stream to obtain a measure of total mercury in such gas sample.

The practice of the instant invention may be effected with a quartz-lined or a PFA or PTFE Teflon lined extractive probe inserted into the flue stack to withdraw a sample of the exhaust stream. To minimize particulate contamination of the reactor zone, the extractive sampling should be located after an exhaust stacks particulate removal device. Further, particulate removal at the extractive probe can be accomplished by a filter which should have a pore size smaller than the particulates found in the input gas stream and preferably less than about 0.5 microns. The reactor zone is positioned proximal to the extractive probe. The flow of the extracted sample gas can be directed either through or around the reactor zone to the detector which may be placed up to as much as 100 feet from the extraction point. The line in which the sample gas flows to the detection instrument is heated and insulated and may be comprised of PFA OR PTFE Teflon having, for example, an I.D. of about 1.2 cm. Since mercury species will interact with steel surfaces, if the gas cell in the measuring instrument is steel, it should be retrofitted with a quartz liner to prevent such interactions. Alternatively, other materials which are nonreactive with mercury may be used such as, for example, PFA or PTFE Teflon. A quartz-lined steel cell provides a more durable instrument than one with a quartz cell alone.

The reactor zone used in some of our early work comprised a quartz cell sized from 20 to 50 cm in length and about 1.9 cm in diameter. At the longitudinal center of the quartz cell a Nichrome® heating element was wound around the outside of the quartz cell for a length of about 12 to 15 cm with each of the turns spaced so as not to touch one another. The temperature at this center of the quartz cell or hot zone of the reactor was maintained in the range from 750° to 900° C. in order to reduce $HgCl_2$ into its components, $Hg(O)$ and $Cl_2$. Within the quartz cell, a smaller quartz cell of about ⅓ the I.D. of the outer cell was concentrically positioned so that the outlet of the smaller quartz cell was at about the longitudinal center of the thermal reactor zone, i.e., under or substantially under the Nichrome® heating element. This inside and concentric tube was used to introduce a stream of hydrogen gas, which exited directly into the center or hot zone of the reactor, at a volumetric flow rate such that about two volumes of hydrogen was introduced for each volume of oxygen contained in the gas sample. The oxygen concentration may be determined by any suitable oxygen monitor. If the oxygen concentration varies widely, a monitored oxygen concentration response could be continuously fed to a control valve designed to vary the hydrogen flow accordingly. Prior to the initiation of hydrogen flow into the reactor zone, the concentrically placed hydrogen feed-line was purged of any air which may have accumulated therein. Also, this hydrogen feed-line was in the form of a capillary tube to ensure sufficiently high laminar velocity so as to reduce flash-back of burning hydrogen back up the feed line. Also, since the amount of additional hydrogen necessary for reaction with the small amounts of chlorine gas are minor amounts, the simplest way to adjust for same is to add a slight excess of hydrogen over that determined necessary to react with the oxygen, i.e., perhaps about 1% to about 5%, it being understood that, if desired for some presently unknown reason, a greater excess of hydrogen may be utilized. The temperature of the reactor zone was brought to approximately 800° C., the hydrogen was bled into the reactor zone and the water vapor resulting therein was condensed and removed prior to introducing the gas stream into a suitable detector where the $Hg(O)$ was measured in a stream of dry gas.

EXAMPLE

In order that those skilled in the art may better understand how the present invention may be practiced, the following example is given by way of illustration only and not necessarily by way of limitation, since numerous variations thereof will occur and will undoubtedly be made by those skilled in the art without substantially departing from the true and intended scope and spirit of the instant invention herein taught and disclosed.

The measurement instrument which was used in this example comprising the tests listed in TABLE 1, below was a UV monitoring system of the type described in U.S. Pat. No. 3,306,156, Glasser et al., Feb. 28, 1967. The photometer was modified and specially configured to measure mercury in the presence of sulfur dioxide at 254 nm. The instrument was calibrated for 1 ppb elemental mercury and 1500 ppm sulfur dioxide and was found to accurately measure elemental mercury at values as low as 0.2 ppb±0.1 ppb. The 20 cm stainless steel gas sample cell used with this instrument was quartz lined.

The following example demonstrates that a hydrogen flow introduced into the reactor zone can maintain mercury in its reduced state so that a measurement of total mercury was accomplished. The thermal conversion cell used herein was 20 cm long with an O.D. of 1.9 cm and an I.D. of 1.5 cm through which the gas sample flowed. The hydrogen gas flowed through a concentrically placed quartz cell of about 0.5 cm O.D. and 0.3 cm I.D. and exited at about the longitudinal center of the reactor zone. The reactor zone was defined by the placement of a Nichrome® element that was wound around a 12 cm length of the outside tube. The reactor zone is the longitudinal center of the Nichrome® wrapped region.

The process was tested by generating a known, measured amount of $HgCl_2$ and mixing this gas with various other flue gas components, such as HCl, $O_2$, $CO_2$, $SO_2$, NO, $NO_2$, $H_2$, $N_2$ and $H_2O$, and passing the gaseous mixtures through the reactor and monitoring the $Hg(O)$ response with the measuring instrument and comparing those responses to that of the baseline reduction of $HgCl_2$ to $Hg(O)$ in nitrogen and water vapor. All tests listed were run with an 8% water vapor concentration.

The known, measured amount of $HgCl_2$ was delivered by a $HgCl_2$ generation tube obtained from VICI Metronics and calibrated on the gas-line system. When the $HgCl_2$ generation tube was heated to 80° C. in an oil bath it generated a quantity of $HgCl_2$ which corresponded to 0.65 ppb $Hg(O)$ when thermally reduced. The effect of various flue gas components on the efficiency of thermal reduction of $HgCl_2$ was observed from the following instrument responses tabulated in TABLE 1, below. The results of tests a–c illustrate that thermal reduction (at 800° C.) of the resulting generated $HgCl_2$ in the presence of nitrogen and 8% water vapor produced a UV response which corresponds to 0.65 ppb $Hg(O)$ indicating 100% reduction of $HgCl_2$ to $Hg(O)$. The results of tests d–f show that HCl and $O_2$ reduced the effectiveness of the thermal reduction process but their interference was alleviated by the introduction of hydrogen in a volumetric ratio of 2:1 with respect to oxygen in the sample. In tests g–j, $SO_2$ and $CO_2$ were added to the gaseous mixture but the effectiveness of the conversion was only significant when the hydrogen:oxygen volumetric ratio was 2. In tests k–q NO and $NO_2$ were added to the reduction process and again the effectiveness of the mercury reduction is maintained only when the hydrogen:oxygen volumetric ratio was 2. The data show that the reduced form of mercury could be maintained in the gaseous matrix when 2 volumes of hydrogen per volume of oxygen was introduced into the reactor zone of the conversion cell. Assuming both $H_2$ and $O_2$ act as ideal gases, the volumetric ratio can be considered the same as the mole ratio.

TABLE 1

| Test | HCl ppb | $O_2$% | $CO_2$% | $SO_2$ ppm | NO ppm | $NO_2$ ppm | $H_2$ ml/min | Response ppb Hg(0) |
|---|---|---|---|---|---|---|---|---|
| a | 0 | 0 | 0 | 0 | 0 | 0 | 0 | 0.65 |
| b | 0 | 0 | 0 | 0 | 0 | 0 | 0 | 0.65 |
| c | 0 | 0 | 0 | 0 | 0 | 0 | 0 | 0.63 |
| d | 68 | 7 | 0 | 0 | 0 | 0 | 0 | 0.31 |
| e | 68 | 7 | 0 | 0 | 0 | 0 | 120 | 0.24 |
| f | 68 | 7 | 0 | 0 | 0 | 0 | 250 | 0.66 |
| g | 68 | 7 | 14 | 800 | 0 | 0 | 0 | 0.22 |
| h | 68 | 7 | 14 | 800 | 0 | 0 | 100 | 0.55 |
| i | 68 | 7 | 14 | 800 | 0 | 0 | 200 | 0.58 |
| j | 68 | 7 | 14 | 800 | 0 | 0 | 300 | 0.61 |
| k | 68 | 7 | 14 | 800 | 525 | 30 | 0 | −0.03 |
| l | 68 | 7 | 14 | 800 | 525 | 30 | 0 | −0.09 |
| m | 68 | 7 | 14 | 800 | 525 | 30 | 100 | 0.53 |
| n | 68 | 7 | 14 | 800 | 525 | 30 | 200 | 0.58 |
| o | 68 | 7 | 14 | 800 | 525 | 30 | 300 | 0.67 |
| p | 68 | 7 | 14 | 800 | 525 | 30 | 300 | 0.62 |
| q | 68 | 7 | 14 | 800 | 525 | 30 | 300 | 0.64 |

INVENTION PARAMETERS

After sifting and winnowing through the data supra, as well as other results and operations of our instant new, novel, and improved technique, including methods and means for the effecting thereof, the operating variables, including the acceptable and preferred conditions for carrying out the instant invention are summarized below:

| VARIABLES | OPERATING LIMITS | PREFERRED LIMITS | MOST PREFERRED LIMITS |
|---|---|---|---|
| Temp of Thermal Reactor zone | 300–1000° C. | 750–850° C. | 800° C. |
| Water Vapor Conc.* | 0–50% | 5–10% | 7–8% |
| $SO_2$ Conc.* | 0–2500 ppm | 0–2000 ppm | 0–1500 ppm |
| HCl Conc.* | 0–2% | 0–300 ppm | 20–150 ppm |
| Sample Flow Rate* | 1–3 L/min | 1.8–2.2 L/min | 2 L/min |

*Those variables refer to composition or characteristic of sample stream prior to flow through the thermal conversion unit, i.e., the reactor.

While we have shown and described particular embodiments of our invention, modifications and variations thereof will occur to those skilled in the art. We wish it to be understood therefore that the appended claims are intended to cover such modifications and variations which are within the true scope and spirit of our invention.

What we claim as new and desire to secure by Letters Patent of the United States is:

1. An improved system for the thermal reduction, in sampled gases, of mercury chloride to elemental mercury prior to determination of total mercury in such sampled gases, and said sampled gases comprising, in addition to said mercury chloride, gaseous impurities characterized by their propensity to effect oxidation of said elemental mercury, said gaseous impurities comprising $Cl_2$, $O_2$, HCl, $H_2O$, and mixtures thereof, said improved system comprising:

collection means for collecting a gas sample;

filtration means operatively associated with said collection means for removing particulates from said collected gas sample;

reaction means operatively associated with said filtration means for reducing in said collected and filtered gas sample gaseous mercury chloride to gaseous elemental mercury and chlorine vapor, said reaction means having a hot zone therein capable of being heated to at least about 800° C.;

gas inlet means for introducing hydrogen gas into said hot zone of said reaction means;

gas outlet means for removing reaction products from said reaction means and introducing said removed reaction products to condensation means, said condensation means disposed for removing water vapor comprised in said reaction products introduced thereinto, said water vapor containing hydrochloride vapor dissolved therein, and said water vapor formed in situ in said hot zone; and photometric measurement means operatively associated with said condensation means for measuring the intensity of Hg(O) radiation in the resulting water vapor and HCl depleted gas sample.

2. The improved system of claim 1, wherein said photometric measurement means comprises an ultraviolet spectrophotometer.

3. The improved system of claim 2, wherein said UV spectrophotometer comprises a UV spectrophotometer which effects elemental mercury determination at 254 nm.

4. The improved system of claim 1, wherein said collecting means comprises an extraction probe.

5. The improved system of claim 1, wherein said reaction means comprises a quartz cell designed to mix the sampled gas with a predetermined amount of hydrogen gas stoichiometrically sufficient to react with oxygen and chlorine gases in said collected gas sample.

6. The improved process for the determination in flue gases or the like of total mercury concentration and the distribution of its oxidized specie Hg(II) and its reduced specie Hg(O) therein, said flue gas comprising in addition to said mercury species as pollutants measurable quantities of $O_2$, $H_2O$, HCl, $Cl_2$, and mixtures thereof, said improved process comprising the steps of:

(1) capturing a predetermined quantity of said flue gas as a sample;

(2) removing particulates from said sample;

(3) introducing a first portion of said sample into detection means, said detection means calibrated for effecting the quantitative determination of Hg(O);

(4) introducing a second portion of said sample into reactor means;

(5) simultaneously introducing into said reactor means a predetermined quantity of hydrogen;

(6) admixing said second portion of said sample and said hydrogen in said reactor means wherein the resulting mixture is maintained at a temperature of at least about 750° C. for at least about one second;

whereby the quantity of hydrogen introduced is sufficient to combine with the free oxygen therein to form water vapor and wherein sufficient additional hydrogen is provided to combine with free chlorine therein to form hydrogen chloride, and further wherein said hydrogen chloride is absorbed in said water vapor, and still further wherein the oxidized mercury is reduced to elemental mercury, said reaction of oxygen and chlorine with hydrogen substantially preventing reoxidization of said resulting elemental mercury;

(7) removing at least a portion of the reaction products from said reactor means and introducing same into water trapping means for removing therefrom the hydrogen chloride containing water vapor;

(8) removing at least a portion of the resulting reaction products from said water trapping means and introducing same into detection means calibrated for the quantitative determination of Hg(O) and effecting such determination of Hg(O); and (9) comparing such determination of Hg(O) effected in step (8), supra, with the determination of Hg(O) effected in step (3), supra, for determination of total mercury and the distribution of its oxidized form relative to its reduced form.

7. The process of claim 6, wherein steps (4)–(8) are practiced before the practice of step (3), and where, in step (9) the comparison is between the determination subsequently effected in step (3) with the determination previously effected in step (8).

8. The process of claim 7, wherein the temperature in said reactor means is maintained in the range from about 800° C. to about 1000° C.

9. The process of claim 6, wherein the temperature in said reactor means is maintained in the range from about 800° C. to about 1000° C.

\* \* \* \* \*